United States Patent [19]

Lou et al.

[11] 4,329,151

[45] May 11, 1982

[54] STABLE DIAGNOSTIC REAGENT AND METHOD FOR QUALITATIVE DETERMINATIONS OF STREPTOCOCCI INFECTIONS

[75] Inventors: Kingdon Lou; Tracey L. Burton, both of Fountain Valley, Calif.

[73] Assignee: ICL Scientific, Fountain Valley, Calif.

[21] Appl. No.: 67,305

[22] Filed: Aug. 17, 1979

[51] Int. Cl.$^3$ ............................................. G01N 33/54
[52] U.S. Cl. .................................... 23/230 B; 23/915; 424/12
[58] Field of Search ................ 23/230 B, 915; 424/12; 260/112 R, 112 B

[56] References Cited

U.S. PATENT DOCUMENTS

| | | | |
|---|---|---|---|
| 3,857,931 | 12/1974 | Hager | 424/12 |
| 3,956,477 | 5/1976 | Price et al. | 23/230 B X |
| 3,985,867 | 10/1976 | Redshaw | 23/230 B X |
| 4,108,974 | 8/1978 | Wegfahrt et al. | 424/12 X |
| 4,181,636 | 1/1980 | Fischer | 424/12 X |

FOREIGN PATENT DOCUMENTS 1914081 10/1970 Fed. Rep. of Germany .

OTHER PUBLICATIONS

Ramello et al., Archivio per le Scienze Mediche, 126, 390-392, 1969.
Ramello et al., "Determination of Anti-O-Streptolysin titer with Polystyrene Latex", Chemical Abstracts, vol. 73, No. 1975r, 1970.
Kumagai et al., "Reagents for Rapid Antistreptococcal Antibody Tests", Chemical Abstracts, vol. 80, No. 131627j, 1974.
Mosley et al., "BSSA: AN Agglutinogen for Quantitation of Antistreptolysin-O", Amer. Journal of Clincal Pathology, vol. 44, No. 5, Nov. 1965.

Primary Examiner—Arnold Turk
Attorney, Agent, or Firm—Fulwider, Patton, Rieber, Lee & Utecht

[57] ABSTRACT

A method and a stable reagent for the detection of pathogenic bacterial infections in humans, and in particular, a stable diagnostic composition comprising non-degraded streptolysin-O protein directly adsorbed onto polystyrene latex particles and method of use are disclosed. The reagent may be prepared by adsorbing one or more layers of the streptolysin-O toxin onto the surface of the latex particle, effecting an intermolecular cross-linkage of the streptolysin-O, and further stabilizing the reagent by the addition of a bacteriostatic agent. Accordingly, the present invention provides a significant advance regarding the qualitative determinations of streptococci infections by providing a stable diagnostic reagent and method for such determinations.

20 Claims, No Drawings

STABLE DIAGNOSTIC REAGENT AND METHOD FOR QUALITATIVE DETERMINATIONS OF STREPTOCOCCI INFECTIONS

BACKGROUND OF THE INVENTION

The present invention relates to a method and a stable reagent for the chemical diagnosis of a pathogenic bacterial infection in humans. More particularly, the present invention relates to the production of a stable reagent which permits qualitative determination of streptococci infections by unaided visual determination.

When a human or other animal is exposed to foreign proteins of antigenic character, an immunologic response will often occur. One aspect of this response is the presence in the animal's blood of water-soluble antibodies capable of specifically recognizing and binding the foreign protein.

During a bacterial infection in an animal, the invading organisms may excrete a great number of these foreign proteins. Streptococci bacteria have been shown to excrete over 20 exocellular toxins, one of which is a cytolytic protein known as streptolysin-O.

Streptolysin-O is an extremely destructive protein, one of its prime functions being the hemolysis of red blood cells. Fortunately, streptolysin-O is also antigenic and the animal can respond immunologically with the appropriate antibodies (anti-streptolysin) which can inhibit lysogenesis by binding onto the streptolysin-O.

The amount of anti-streptolysin present in serum, called the "titer" is an important tool to clinicians, not only for the diagnosis of streptococci infection, but also for its relationship with rheumatic fever, acute gloumerulonephritis, rheumatoid arthritis and erythema nodosum. To determine this titer, some technicians have utilized the inhibitory properties of anti-streptolysin in conjunction with the lytic properties of streptolysin-O on red blood cells. In this respect, the study done by Rammelkamp [Am. J. Med. 10:673, 1951] teaches one such method.

The most commonly used method for determining the concentration of streptolysin-O antibodies is to perform a hemolytic inhibition test. One of the activities of the streptolysin-O is its ability to hemolyze human red blood cells and blood cells of other animal species. In the presence of anti-streptolysin in the patient's serum, the hemolysis is inhibited. Thus, an increased concentration of anti-streptolysin present in the serum will be reflected in greater inhibition. Quantitative expression is measured by an elaborate dilution scheme of the patient's serum.

The isolation of streptolysin-O from the culture medium is a long and tedious process. In addition, after several days of handling in an aerobic atmosphere, the toxin is in an oxidized form. For hemolytic activity, streptolysin-O must be in a reduced state. This is usually accomplished by the addition of cysteine, 2-mercaptoethanol or other thiols as reducing agents. Even with the addition of any of these compounds, the hemolytic potency of the toxin is short lived. Commercially available streptolysin-O reagents are usually reduced, freeze dried, and sealed under an inert gas atmosphere. Under reconstitution, the reduced material must be used within thirty minutes.

Although this test procedure is widely used, it is tedious and necessitates maintaining a constant supply of viable red blood cells. Also, because streptolysin-O loses potency when oxidized, the procedure must be done quickly or in the presence of reducing agents which may adversely affect the analysis.

From the literature, it is apparent that streptolysin-O and its activity will form precipitins without the necessity of activating the oxidized toxin. Thus, the indication is that while the hemolytic activity is dependent on the toxin being in a reduced form, the precipitin formation is independent of its redox state.

Antigen-antibody reactions may manifest themselves under various conditions. In soluble forms, the antigen and antibodies will combine to form loose aggregates, which continue to a lattice build-up to become visible precipitates. If this soluble antigen-antibody reaction should take place in a semi-solid medium such as agar, a macroscopically visible precipitin line will result.

Attempts to simplify the foregoing test procedure have been based on the well-known antibody agglutination process and the fact that anti-streptolysin recognition of streptolysin-O is independent of the toxin's redox state. In addition, due to the importance of qualitative determination of anti-streptolysin titers, much research has been directed towards rendering the agglutination product macroscopically visible.

The conversion of a "precipitin" reaction to an "agglutination" reaction has occupied the time and efforts of clinical immunochemists throughout the world for the past three decades. Adsorption of a reactant to a carrier particle serves to demonstrate the presence of either the antigen or antibody within a relatively short length of time, and secondly, the macroscopic visualization of the antigen-antibody reaction does not require the need for elaborate or sophisticated equipment. For these reasons, simple agglutination reactions have enjoyed wide popularity in laboratory use of immunodiagnosis of disease states. Various carrier particles such as erythrocytes, bentonite, collodium, quartz, synthetic resins and latex particles have been employed as the serologic carrier of one of the reactants.

In instances of antigen-antibody reaction, where the reactant is in a particulate form, visible agglutination of the particles will demonstrate the antibody-antigen reaction.

Technical difficulties, availability, variation in sizes and compositions have eliminated many of the aforementioned carriers as reactant particles. However, commercially available uniform size polystyrene latex has enjoyed immense popularity as a serologic carrier.

Various techniques for forming visible agglutination products in general are known in the art and good results have been obtained by adsorbing either the antigen or the antibody to a carrier. In this regard, U.S. Pat. No. 3,088,875 teaches the use of polymerized styrene latex particles as carriers.

Polystyrene latex particles are usually hydrophobic and negatively charged, and will non-specifically adsorb many proteinaceous materials. However, because the adsorption is often not permanent, a number of procedures have been developed to stabilize the protein-latex complex. These methods usually require some modification of the protein and the addition of extraneous high molecular weight materials. A representative sampling of these procedures can be found in U.S. Pat. Nos. 3,658,982 and 3,992,517, and German Pat. No. 1,914,081.

These polystyrene particles are usually prepared by initiating the polymerization of styrene monomers with potassium persulfate in the presence of the emulsifier sodium laurel sulfate. In preparation of particles through emulsion polymerization the stability of the polystyrene particles is due in part to the charged surface groups originated from the initiator through surface sulfate groups. However, the emulsifier also contributes to the stability of the particles by imparting an electrical negative charge. The greater the quantity of emulsifier the greater the negative charge on the latex particle surface. A double layer of ions and counter ions is usually responsible for the stability of the particles. Divalent and trivalent cations as well as high ionic strength buffers may cause destabilization of the polystyrene latex colloid.

A review of the art reveals that IgG molecules containing antibody activity are usually non-specifically adsorbed onto the polystyrene latex particles which then serve as a reagent. Heat and other methods of denaturation will tend to "stabilize" the reagent. These antibodies, usually composed of negatively charged IgG molecules, will be adsorbed onto the negatively charged latex particles due to the influence of the nonionic van der Waals forces and the hydrophobic bond effects.

When streptolysin-O is combined with polystyrene latex particles by alteration of the protein, either through partial degradation or by the addition of stabilizing materials, the modification may cause a loss of some antigenic determinants and a decrease in assay sensitivity. Furthermore, the extraneous materials utilized may interfere with the antibody-antigen interaction or the agglutination reaction, resulting in false results and incorrect clinical diagnosis.

Thus, those skilled in the art have recognized a significant need for a stable streptolysin-O-latex complex in which the protein retains significant preadsorption characteristics and wherein the entire complex is free from potentially contaminating intermediaries. The present invention fulfills this need.

SUMMARY OF THE INVENTION

The present invention relates to a method and a stable reagent for the detection of pathogenic bacterial infections in humans, and in particular, provides a stable diagnostic composition consisting of non-degraded streptolysin-O protein directly adsorbed onto polystyrene latex particles.

The reagent may be prepared by adsorbing one or more layers of the streptolysin-O toxin onto the surface of the latex particle, effecting an intermolecular cross-linkage of the streptolysin-O, and further stabilizing the reagent by the addition of a bacteriostatic agent.

More specifically, one significant feature of the invention relates to the non-covalent coating of a polystyrene latex particle with streptolysin-O protein by utilizing an alkaline pH to properly orient the determinant groups of the protein, in conjunction with a carbodiimide to effect intermolecular cross-linking. An additional feature of the invention is that it provides for the maintenane of the stability of the streptolysin-O latex complex by utilizing sodium azide, or other suitable bacteriostatic agents such as thimerosal.

One presently preferred embodiment for coating the material onto polystyrene utilizes an inorganic buffer at pH 10.0. The preferred buffer is prepared with Boric Acid-KCl-NaOH at 0.5 M, although freshly prepared carbonate-bicarbonate buffer at pH 10.0, among others, is also suitable. The final latex streptolysin-O reagent is suspended in a 0.05 M Boric Acid-HCl-NaOH buffer, pH 8.2 with 0.1% $NaN_3$, added.

Accordingly, the present invention significantly advances the state of the art regarding the qualitative determinations of streptococci infections by providing a stable diagnostic reagent and method for such determinations.

DESCRIPTION OF THE PREFERRED EMBODIMENTS

A significant feature of the present invention is embodied in a complex consisting of polystyrene latex particles adsorbed with streptolysin-O antigen in an alkaline environment, the adsorption occurring in the presence of carbodiimide. This complex has been shown to be particularly useful for the qualitative determination of streptococci infections in animals because it enhances formation of a visible agglutination product.

While those skilled in the art have not completely understood the interaction between polystyrene particles and proteins, it is believed that absent any covalent coupling between the two materials, the adsorption occurs in the form of an equilibrium reaction, and therefore is susceptible to small changes in pH, temperature, ionic strength or other environmental factors. A change in any one of these factors could cause disassociation of the latex-protein complex and streptolysin-O adsorbed onto polystyrene particles has proven to be partially susceptible to this problem. The addition of other materials to the complex may tend to lessen the chance of disassociation, but also, the addition of other materials to the complex tends to complicate the determination of optimal conditions for assay procedures.

It has been found that if the adsorption is carried out at a relatively high alkaline pH in the presence of carbodiimide, the resulting product is stable and has a minimal number of critical components. The precise structure of the product formed during the reaction is not fully understood; however, it is believed that at the pH utilized, the determinant groups of the streptolysin-O are beneficially arranged to retain a sufficient amount of antigenicity even while being cross-linked by a carbodiimide. It should be noted that carbodiimides are capable of forming covalent bonds between many types of functional groups, including carboxylic acids, amines, alcohols, and thiols. The actual cross-links formed in the present invention could involve one, some, or all of these groups.

Thus, in accordance with the present invention, streptolysin-O protein is diluted in a buffered solution with a pH range of from about 8.5 to about 11.9, but preferably a pH of about 10.0 is utilized. In this respect, it is noted, however, that a relatively small amount of streptolysin-O protein is adsorbed at about pH 8.2 to about pH 8.5. Below about pH 8.2, possibly due to the orientation of the streptolysin-O molecules, an unstable reagent may result, and activity may disappear within a few days. Further, a similar situation was encountered at pH levels above about pH 11.5. One buffer is a freshly prepared carbonate-bicarbonate solution, and preferred buffers are inorganic buffers, such as 0.5 molar Boric Acid-KCl-NaOH. The buffers may be adjusted to the proper pH by any one of well known methods.

The preparation of the streptolysin-O toxin may suitably be prepared in accordance with the following procedure. Streptococcus pyrogenes, group A. American Type Culture collection #12383, is cultivated in a commercially prepared broth medium known as Todd- Hewitt broth. The culture medium is enhanced with dextrose to promote the production of the streptolysin-O. Following over night growth, the pH of the culture is adjusted with sodium hydroxide to neutralize the acid formed. Additional dextrose is added and the incubation continued for an additional 6–8 hours. The culture is then frozen at −40° C. for 24 or more hours, then thawed at +5°. The top one-third of the thawed culture is collected and centrifuged to remove the bacteria. Solid ammonium sulfate is added to the centrifuged concentrate to a final concentration of 75%. The streptolysin-O is precipitated by the ammonium sulfate. The precipitate is suspended in water, and dialyzed continuously to remove the precipitant.

The isolated streptolysin-O is assayed by preparing two-fold dilutions of the streptolysin-O in a 0.01 M cysteine-HCl solution. To each tube is added 0.2 ml of a 5% suspension of thrice-washed human or sheep erythrocytes suspended in phosphate buffer saline, pH 6.6. The tubes are incubated in a 37° C. water bath for two hours, and the tubes are centrifuged. The end point is the greatest dilution displaying hemolysis of the cells. This is usually 1:2048 dilution, the range being 1:512 to 1:4096.

In this regard, streptolysin-O protein may be prepared according to the general method of J. E. Alouf and M. Raynaud, Biochimie, 55,1187, (1973), which method is incorporated herein by reference, or may be purchased commercially. Alternatively, the streptolysin-O protein may be prepared from standard reagents which are available for hemolysis-inhibition tests. These reagents require concentration before use, for instance, about one thousand fold. The crude streptolysin material may be filtered through a 0.22μ porosity cellulose membrane filter as a sterilizing procedure.

When a new lot of streptolysin-O protein has been prepared for coating the polystyrene latex particles, a suitable formulation procedure is used to prepare reagents containing varying amounts of streptolysin-O attached to the particles. Each reagent may thus be tested with a panel of positive and negative serums, the serums having been tested by hemolysis inhibition and assigned values in Todd or International units. The formulation of streptolysin-O protein chosen may vary, and the preferred formulation giving proper reactivity with the panels may then be used to prepare large amounts of reagents.

In a presently preferred embodiment, the suitably diluted protein is mixed with a 10% (w/v) solution of uniform sized polystyrene latex particles dispersed in deionized water, and an 0.2% (w/v) aqueous solution of water soluble carbodiimide. In this regard, the carbodiimide solution must be freshly prepared and used after solubilization. After mixing from about 12 to about 20 hours, the sensitized particles are washed with a suitable buffer, such as 0.05 M Boric Acid-KCl-NaOH buffer at pH 8.2, and then centrifuged down at 10,000 rcf. This washing procedure is repeated as required, for instance, three times, whereafter the particles are finally re-suspended in the same buffer. A suitable bacteriostatic agent, preferably sodium azide, is then added to achieve an 0.1% (w/v) concentration although a useful range is from about 0.05% (w/v) to 2.0% (w/v).

Another suitable bacteriostatic agent which can be utilized in the preparation of the latex-streptolysin-O reagent is thimerosal. In this respect, it was determined that in terms of being a bacteriostat, thimerosal was found to be effective at 4° C. and 32° C. in the concentration range of from about 0.001% to about 0.00001%. Malachite green dye (C. I. No. 42000) may be added, if desired, to a final concentration of 0.001% (w/v) to enhance the stability and facilitate visual determination of agglutination. For further disclosure of this particular dye and other suitable dyes, reference may be had to the treatise entitled "Conn's Biological Stains", including pages 168, et seq.

The size of the particles, available commercially from Dow Chemical Company, Midland, Mich., may vary from about 0.5 microns to about 7.0 microns, but a uniform size of about 0.62 microns is optimal because of reduced centrifugation time, better separation of the latex-protein complex from other materials during the washing procedure and reproducibility of results.

Suitable water soluble carbodiimides are 1-ethyl-3-(3-dimethylaminopropyl) hydrochloride carbodiimide, available from Ott Chemical Company, Muskegon, Mich., or 1-cyclohexyl-3-(2-morpholinoethyl)-carbodiimide morpho-p-toluenesulfonate, available from Aldrich Chemical Company, Milwaukee, Wis., the latter being preferable. The concentration of the carbodiimide added may vary from about 0.1% (v/w) to about 0.6% (v/w).

The following are illustrative examples of the reagent preparation in accordance with the present invention.

EXAMPLE I

Upon obtaining a 50% concentration of streptolysin-O (1:2048 potency), 10 mls. of Streptolysin-O is added to 10 mls. of a pH sensitizing buffer. Following the addition of 2.0 mls. of 10% (v/w) polystyrene latex to the mixture, 20.0 mls. of 0.2% (v/w) carbodiimide is added. The mixture is stirred over night, and the sensitized particles are washed three times with pH 8.2 buffer. The reagent is re-suspended in 20.0 mls of pH 8.2 buffer with 0.1% sodium azide added.

EXAMPLE II

Upon obtaining a 60% concentration of streptolysin-O, add 12.0 mls of Streptolysin-O to 8.0 mls. of pH 10 sensitizing buffer. 2.0 mls of the 10% (v/w) polystyrene latex dispersion is added and 20.0 mls of 0.2% (v/w) carbodiimide solution combined to form a mixture. The mixture was stirred over night and then washed three times with pH 8.2 buffer. Re-suspend the product in 20.0 mls with pH 8.2 buffer and then add 0.1% sodium azide.

In accordance with the present invention, the test for anti-Streptolysin utilizing the streptolysin-O-latex complex may be performed as follows: The test serum is diluted with normal saline (0.85% w/v NaCl solution in $H_2O$) to a concentration of 1:20, that is one part serum plus 19 parts saline. (This dilution was chosen because it represents the approximate equivalence of 166 Todd units or 200 International Units, both of which are classified as indicative of normal values of anti-streptolysin). One drop of the diluted serum is mixed with one drop of the streptolysin-O-latex complex on a glass slide. The slide then is tilted from side to side through several planes for about three minutes. The presence of a macroscopically visible agglutination product at the end of this time is indicative of an anti-streptolysin titer greater than 166 Todd units (or 200 International Units).

The following Tables I–III show the results of clinical tests comparing quantitative values of anti-streptolysin titer with results obtained using the ASO slide test in accordance with the present invention:

TABLE I

| | LABORATORY # | ASO TITER | ASO SLIDE TEST |
|---|---|---|---|
| 1. | 3570-1 | 50 | Negative |
| 2. | 3571-1 | 80 | Negative |
| 3. | 3606-1 | 80 | Negative |
| 4. | 3621-1 | <25 | Negative |
| 5. | 3626-1 | 50 | Negative |
| 6. | 3702-2 | 80 | Negative |
| 7. | 3714-2 | 25 | Negative |
| 8. | 3779-1 | 80 | Negative |
| 9. | 3837-1 | <25 | Negative |
| 10. | 3852-1 | 50 | Negative |
| 11. | 3853-1 | 80 | Negative |
| 12. | 3995-1 | 50 | Negative |
| 13. | 4000-1 | 25 | Negative |
| 14. | 4000-2 | 50 | Negative |
| 15. | 4001-1 | 25 | Negative |
| 16. | 4001-2 | 50 | Negative |
| 17. | 4003-1 | 80 | Negative |
| 18. | 4448-1 | 50 | Negative |
| 19. | 4451-2 | 80 | Negative |
| 20. | 3779-3 | 80 | Negative |
| 21. | 3995-2 | 80 | Negative |

21 Sera - ASO titer range - <25-80
ASO SLIDE TEST 21/21 Negative

TABLE II

| | LABORATORY # | ASO TITER | ASO SLIDE TEST |
|---|---|---|---|
| 1. | 3593-1 | 100 | Negative |
| 2. | 3574-1 | 120 | Negative |
| 3. | 3590-1 | 120 | Positive |
| 4. | 3593-2 | 100 | Positive |
| 5. | 3602-3 | 100 | Negative |
| 6. | 3626-2 | 160 | Positive |
| 7. | 3642-2 | 120 | Positive |
| 8. | 3643-2 | 100 | Negative |
| 9. | 3665-1 | 160 | Negative |
| 10. | 3739-1 | 100 | Negative |
| 11. | 3743-2 | 120 | Negative |
| 12. | 3743-3 | 100 | Negative |
| 13. | 3861-1 | 100 | Negative |
| 14. | 3880-1 | 100 | Negative |
| 15. | 3956-1 | 100 | Negative |
| 16. | 3964-1 | 100 | Negative |
| 17. | 3977-1 | 100 | Negative |
| 18. | 3977-2 | 160 | Negative |
| 19. | 3991-2 | 120 | Negative |
| 20. | 3853-3 | 120 | Negative |
| 21. | 3777-1 | 160 | Negative |
| 22. | 3833-2 | 160 | Negative |
| 23. | 3896-2 | 160 | Negative |

23 Sera - 100-160 ASO Range
ASO SLIDE TEST 4/23 Positive

TABLE III

| | LABORATORY # | ASO TITER | ASO SLIDE TEST |
|---|---|---|---|
| 1. | 3617-3 | 200 | Positive |
| 2. | 3739-2 | 240 | Positive |
| 3. | 3739-3 | 460 | Positive |
| 4. | 3774-2 | 240 | Positive |
| 5. | 3774-3 | 240 | Positive |
| 6. | 3846-3 | 200 | Positive |
| 7. | 3872-3 | 200 | Positive |
| 8. | 3929-1 | 200 | Positive |
| 9. | 3936-1 | 400 | Positive |
| 10. | 3965-2 | 240 | Positive |
| 11. | 4040-3 | 480 | Negative |
| 12. | 4453-2 | 200 | Positive |
| 13. | 4453-2 | 320 | Positive |
| 14. | 4477-2 | 240 | Positive |
| 15. | 4507-2 | 400 | Positive |
| 16. | 4547-2 | >640 | Positive |

16 Higher titer sera
200->640
15/16 Positive by ASO Slide Test

The following table shows the results of clinical tests comparing the hemolytic titer values from another commercially available test in accordance with German Pat. No. 1,914,081 assigned to Behring, and results obtained using the present invention.

TABLE IV

ASO CLINICAL TEST PROTOCOL RESULTS

| SPECIMEN IDENTIFICATION | ASO SLIDE TEST | HEMOLYTIC TITER | TEST IN ACCORDANCE WITH GERMAN PATENT NO. 1,914,081 |
|---|---|---|---|
| 841 | Weak Positive | 500 T.U. | Positive |
| 938 | Negative | 166 | Negative |
| 952 | Negative | 12 | Negative |
| 972 | Negative | 50 | Negative |
| 002 | Negative | 50 | Negative |
| 016 | Negative | <12 | Negative |
| 78 | Positive | 166 | Negative |
| 89 | Positive | 166 | Positive |
| 130 | Negative | 50 | Negative |
| 210 | Weak Positive | 166 | Negative |
| 256 | Negative | 50 | Negative |
| 266 | Negative | 12 | Negative |
| 969 | Positive | 333 | Positive |
| 82 | Negative | 166 | Positive |
| 92 | Negative | 50 | Negative |
| 118 | Negative | 12 | Negative |
| 126 | Negative | 100 | Negative |
| 254 | Negative | 50 | Positive |
| 311 | Negative | 12 | Negative |
| 405 | Negative | 50 | Negative |
| 409 | Weak Positive | 100 | Negative |
| 553 | Negative | 166 | Positive |
| 588 | Negative | 50 | Negative |
| 640 | Negative | 50 | Negative |
| 651 | Negative | <12 | Negative |
| 443 | Negative | 125 | Negative |
| 687 | Negative | 12 | Negative |
| 694 | Negative | 50 | Negative |
| 474 | Negative | 250 | Negative |
| 611 | Negative | 50 | Negative |
| 693 | Negative | <12 | Negative |
| 713 | Positive | 50 | Negative |
| 56 | Negative | 125 | Negative |
| 63 | Negative | <12 | Negative |
| 92 | Negative | 50 | Positive |
| 376 | Negative | 50 | Negative |
| 388 | Positive | 33 | Positive |
| 469 | Negative | 12 | Negative |
| 481 | Negative | 12 | Negative |
| 487 | Negative | 12 | Negative |
| 499 | Positive | 166 | Positive |
| 514 | Positive | 166 | Positive |
| 527 | Negative | 12 | Negative |
| 571 | Positive | 50 | Negative |
| 602 | Positive | 250 | Positive |
| 605 | Negative | <12 | Negative |
| 610 | Positive | 250 | Positive |
| 674 | Negative | <12 | Negative |
| 686 | Negative | 50 | Negative |

Accordingly, the present invention fulfills the significant need for a stable streptolysin-O-latex complex in which the protein substantially retains pre-adsorption charcteristics and the entire complex is free from potentially contaminating intermediaries, thereby providing improved sensitivity and ease of qualitative determinations.

We claim:

1. A stable reagent for the chemical diagnosis of pathogenic bacterial infections in humans and, in particular, for the qualitative determination of streptococci infections in human serum, the reagent comprising a substantially uniform polystyrene latex particle, said particle being directly adsorbed at a pH between about 8.5 and 10.9 with a cross-linked streptolysin-O protein coating and stabilized with a bacteriostatic agent, said coating being characterised in that it is substantially free from adsorption facilitating extraneous macromolecules.

2. The reagent as defined in claim 1, wherein the average diameter of said polystyrene latex particle is from about 0.5 microns to about 0.7 microns.

3. The reagent as defined in claim 1, wherein said cross-linked streptolysin-O protein coating is formed between functional groups capable of reacting with water-soluble carbodiimide.

4. The reagent as defined in claim 1, wherein said bacteriostatic agent is sodium azide having concentration range of from about 0.05% (w/v) to about 2.0% (w/v).

5. The reagent as defined in claim 1, wherein said bacteriostatic agent is sodium azide having a concentration of about 0.10% (w/v).

6. The reagent as defined in claim 1, wherein said bacteriostatic agent is thimerosal having a concentration range of from about 0.00001% (w/v) to about 0.001% (w/v).

7. The reagent as defined in claim 1, said coating further including a biological stain.

8. The reagent as defined in claim 7, wherein said biological stain is Malachite green.

9. A method for producing a stable diagnostic reagent having a coating of non-degraded streptolysin-O protein directly adsorbed onto a polystyrene latex particle, the method comprising the addition of the polystyrene latex particle, streptolysin-O protein and a water soluble carbodiimide to a buffered solution having a pH of from about pH 8.5 to about pH 11.9, stirring the resultant mixture for a sufficient period of time to form a sensitized particle having a non-degraded streptolysin-O protein coating, washing this sensitized particle and stabilizing said streptolysin-O coating by re-suspension of the sensitized particle in a buffered solution of a bacteriostatic agent.

10. The method in claim 9, wherein said buffered solution is formed from an inorganic buffer.

11. The method in claim 9 wherein said buffered solution has a pH of about pH 10.

12. The method in claim 9 wherein said buffer is Boric Acid-KCl-NaOH.

13. The method in claim 9 wherein said carbodiimide is selected from the group consisting of 1-cyclohexyl-3-(2-morpholinoethyl)-carbodiimide morpho-p-toluene-sulfonate and 1-ethyl-3-(3-dimethylaminopropyl) carbodiimide hydrochloride.

14. The method in claim 9 wherein said bacteriostatic agent is sodium azide.

15. The method in claim 14 wherein said sodium azide is present in a concentration range of from about 0.05% (w/v) to about 2.0% (w/v).

16. The method in claim 9 wherein said bacteriostatic agent is thimerosal.

17. The method in claim 16 wherein said said thimerosal is present in a concentration range of from about 0.00001% (w/v) to about 0.001% (w/v).

18. The method in claim 9 and further including the addition of a biological stain to said buffered solution.

19. The method in claim 18 wherein said biological stain is Malachite green.

20. A method for the chemical diagnosis of pathogenic bacterial infections in humans, and, in particular, for the qualitative determination of streptococci infections in human serum, the method comprising the steps of:
providing a stable reagent comprising a substantially uniform polystyrene latex particle, said particle being directly adsorbed at a pH between about 8.5 and 11.9 with a cross-linked streptolysin-O protein coating and stabilized with a bacteriostatic agent, said coating being characterized in that it is substantially free from adsorption facilitating extraneous macromolecules;
standardizing a solution of said streptolysin-O-polystyrene latex reagent to allow agglutination to occur when one drop of the solution is added to a 1:20 dilution of human serum containing antistreptolysn-O;
diluting one part of the human serum to be tested with 19 parts of normal saline;
mixing one drop of streptolysin-O-polystyrene latex reagent solution with one drop of human test serum on a suitable substrate, and
visually determining the occurrence of a macroscopic agglutination product.

* * * * *

UNITED STATES PATENT AND TRADEMARK OFFICE
CERTIFICATE OF CORRECTION

PATENT NO. : 4,329,151
DATED : May 11, 1982
INVENTOR(S) : Lou et al.

It is certified that error appears in the above—identified patent and that said Letters Patent is hereby corrected as shown below:

Col. 3, line 66, "0.5M" should be -- 0.05M --.

Signed and Sealed this

Twenty-fourth Day of August 1982

[SEAL]

Attest:

GERALD J. MOSSINGHOFF

Attesting Officer — Commissioner of Patents and Trademarks